United States Patent [19]
Stephenson

[11] Patent Number: 6,019,551
[45] Date of Patent: Feb. 1, 2000

[54] EXTRACTING SYSTEM AND METHOD

[75] Inventor: Everett H. Stephenson, Savannah, Ga.

[73] Assignee: Internatioal Paper Company, Tuxedo, N.Y.

[21] Appl. No.: 09/159,050

[22] Filed: Sep. 23, 1998

Related U.S. Application Data

[63] Continuation-in-part of application No. 08/935,432, Sep. 23, 1997.

[51] Int. Cl.[7] .................................................. B23B 39/00
[52] U.S. Cl. .............................. 408/92; 408/138; 408/204
[58] Field of Search ................................ 408/138, 112, 408/137, 92, 204, 101

[56] References Cited

U.S. PATENT DOCUMENTS

| | | | |
|---|---|---|---|
| 344,566 | 6/1886 | Cluever | 408/138 |
| 833,001 | 10/1906 | Press | 408/138 |
| 3,707,043 | 12/1972 | Jones | 408/138 |
| 4,468,159 | 8/1984 | Oster | 408/112 |
| 5,051,044 | 9/1991 | Allen | 408/92 |
| 5,797,708 | 8/1998 | Bencic | 408/112 |

*Primary Examiner*—Andrea L. Pitts
*Assistant Examiner*—Adesh Bhargava
*Attorney, Agent, or Firm*—Synnestvedt & Lechner LLP

[57] ABSTRACT

An extractor comprising (a) a frame being configurable in an extracting position having a front and back orientation; and (b) an extractor assembly mountable to said frame for imparting a backward urging force against a drill bit lodged within said object.

19 Claims, 10 Drawing Sheets

EXTRACTING SYSTEM AND METHOD

REFERENCE TO A RELATED CASE

This is a continuation-in-part of application Ser. No. 08/935,432 filed Sep. 23, 1997, hereby incorporated by reference.

FIELD OF INVENTION

The present invention relates generally to boring or drilling objects. More specifically, the invention relates to a system and method for high torque boring or drilling of large objects, such as trees, with long and/or large diameter drill bits, and to a system and method for extracting the drill bit if it becomes lodged in the object.

BACKGROUND OF THE INVENTION

Many applications require drilling or boring into large objects with long, often thick, drill bits to create a bore hole or to retrieve a core sample of the object. As used herein, the term "drill bit" refers to drill bits, augers, hole cutters, boring bits, coring bits, screws and any other substantially cylindrical device which penetrates a material through rotational motion. The term "drilling" refers to drilling, boring, coring or otherwise advancing a rotating drill bit into an object.

An example of one such drilling application is in the field of forestry where core samples are taken from trees for analysis purposes. The analysis may involve simple determinations such as tree age, growth rate, and penetration of chemicals, in which case, relatively small diameter cores are adequate, or it may entail more sophisticated evaluations such as wood anatomy, wood properties, and data collection for tree breeding program (specific gravity, fiber length and angle, etc.), in which case, larger cores, typically 12 mm (½"), are required.

Manual tools for extracting core samples of wood are used commonly by foresters and technicians. The conventional coring tool uses a tubular bit with a tapered, external thread machined on a short, leading section of the tip which is sharpened with a single, peripheral bevel on the exterior. Coring bits are available in various lengths. Foresters generally use somewhat longer bits than necessary to reach the center of the largest expected trees. A square section machined on the driven end of the bit engages a T-handle. The T-handle provides leverage for a user to rotate the bit. After the hollow, threaded bit is twisted into the tree or wood to be sampled, the core is extracted from the drill bit typically with an extractor.

Manual coring of a tree or lumber using these tools can be an arduous task. For obtaining relatively small diameter cores, typically 5 to 7 mm in diameter, these tools generally can be started manually, simply by leaning into the tree, pushing on the T-handle, and rotating. Dense woods, slightly dull bits, or repetitive corings, however, tax an individual's strength and endurance. Moreover, manual starting of ½" diameter core bits requires much greater force, generally exceeding the capability of a man leaning into the tool.

Manufacturers of these core tools have developed a fixture for starting them. It consists of a threaded collar which is strapped snugly to the tree with a web harness. Rotating the collar with a large T-handle forces the bit into the tree until its external male thread engages. The starting fixture is then removed, and the core bit is driven through the tree.

Although these fixtures help in starting larger bits, delivering the required torque to the bit remains a strenuous task. For example, the torque required to core large or dense trees with a ½" bit ranges from approximately 50 to approximately 100 lb-ft. with a 2-ft. T-handle. Furthermore, it is often necessary to drill the ½" core bits completely through the tree, not just to its center. Even boring a single tree under these conditions can be tremendously fatiguing. Moreover, since there is no support or guide for these relatively thin-walled, 12 to 18" long core bits, it is easy to bend the bit, especially when "leaning" into the bit to deliver the required torque. Aside from damaging it, bending the drill bit also causes misalignment or a divergence from the bit's intended path. This misalignment may cause the bit to miss the center of the tree, resulting in an unbalanced, and possibly crooked, core sample. The continuous, arduous task of coring trees using these manual drills and their limited success therefore has chilled their acceptance and widespread use.

Several attempts have been made to mechanize the collection of core samples, especially larger diameter cores, using either electrical or hydraulic power tools. These attempts, however, have been met with limited success. Heavy duty electric drills tend to lack sufficient torque and rotate too fast to be safe. Suitable hydraulic tools are not commercially available, and custom-built hydraulic equipment tends to be complicated, expensive, and heavy. Since tree core samples are usually obtained in remote areas, a suitable coring device should be simple to operate, reliable and easily transported. Complicated, heavy equipment which requires maintenance and is prone to failure is clearly not acceptable. Therefore, a need exists for a convenient boring or drilling system that can deliver high torque and initiate boring while maintaining drill bit alignment.

In addition to being labor intensive and generally inconvenient, conventional boring systems lack the means to extract a bit if it becomes lodged in the object being drilled. In the field of forestry, for example, it is common for boring bits to become lodged in trees such that they cannot be backed out or driven forward. This situation arises for example when the bit encounters a hollow pocket or decay wherein the threads of the bit have no bite.

Since the bits used to bore trees cost upwards of $600, there is an economic incentive to extract these bits when they become lodged. To this end, bits are often extricated by falling and splitting the tree. Rivaling the cost of the bit, however, is the cost of the tree. Consequently, when a bit becomes lodged in a tree the decision becomes whether to sacrifice the bit or sacrifice the tree. In either case, a significant asset is lost. Therefore, a need exists for extracting a bit that becomes lodged in the object being drilled, particularly trees, without destroying the object in the removal process.

The present invention fulfills the above-mentioned needs among others.

SUMMARY OF INVENTION

The present invention provides for a system and method of drilling with and extracting relatively large/long drill bits by using the mechanical advantage and flexibility afforded by rigidly-held, removable screw mechanisms.

One aspect of the present invention is the provision of a system for boring or otherwise drilling an object by urging the bit forward into the object through rotational motion while delivering high torque and maintaining drill bit alignment. In a preferred embodiment, the system comprises: (a) a frame having a front and back orientation and being positionable in at least a drilling configuration; and (b) a drive assembly removably mountable to the frame for urging the drill bit forward while the bit rotates. The drive assembly comprises a screw mechanism. Through its screw action, the screw mechanism urges the drill bit forward by converting a portion of the rotational force (supplied by a rotating drive such as a hand-held pipe threader) to an axial force. Preferably, the screw mechanism is removable from the frame when the bit is partially drilled into the object. Additionally, in the preferred embodiment, the drive assembly is configured to allow for the drill bit's unencumbered, forward axial movement during drilling. This way, if the threads of the drill bit "bite" and the bit advances forward through its own rotation, it will not be held back by or otherwise bind with the drive assembly.

Another aspect of the present invention is the provision of a method for drilling an object using the system of the present invention. In a preferred embodiment, the method comprises: (a) mounting the frame to the object; (b) mounting a drive assembly having a screw mechanism on the frame; (c) mounting a drill bit on the frame such that the bit is in communication, either directly or indirectly, with the screw mechanism; and (d) operating the screw mechanism to urge the drill bit forward. If the drill bit is threaded, the screw mechanism may be removed once the bit "bites" and advances on its own. Otherwise, the screw mechanism may be used as the source of the drill bit's forward driving force.

Accordingly, the drilling system and method of the present invention allow a user to accurately drill objects without physical exertion. The frame accurately guides and supports the bit, while the driving assembly provides the axial force necessary for starting and the rotational force necessary for drilling. The user no longer needs to "lean" into the bit to initiate drilling. Once drilling is initiated and the drill bit bites, the removable configuration of the screw mechanism allows the user to remove it and apply the rotating drive directly to the drill bit.

Yet another aspect of the present invention is the provision of a bit extractor that employs the same frame as used for drilling along with means to urge the bit backward. In a preferred embodiment, the extractor comprises (a) a frame being configurable in an extracting position having a front and back orientation; and (b) an extractor assembly mountable to said frame for imparting a backward urging force against a drill bit lodged within said object. The urging force, when constantly applied to the drill bit in a backward direction, tends to urge the bit out as the bit is rotated in reverse of its drilling direction. Preferably, the extractor assembly comprises a screw mechanism, and, thus, is similar in function to the screw mechanism of the drive assembly in that it converts rotational force to an axial force through a screw mechanism.

Yet another aspect of the present invention is the provision of a method of extracting a drill bit lodged in an object using the extractor of the present invention. In a preferred embodiment, the method comprises: (a) installing the extractor assembly on the frame; (b) operating the extractor assembly such that a backward urging force is applied against said drill bit; and (c) rotating said drill bit in reverse of its drilling direction.

Accordingly, the extracting system and method of the present invention allow a user to extract drill bits without sacrificing the tree or object being drilled. The frame holds the extractor assembly secure, while the screw mechanism of the assembly provides the backward urging force necessary to urge the drill bit out to the point where its own threads take hold.

BRIEF DESCRIPTION OF THE DRAWINGS

The invention may best be understood by reference to the following description taken in conjunction with the accompanying drawings, wherein like reference numerals identify like elements, and wherein.

DETAILED DESCRIPTION OF THE PRESENT INVENTION

Figure 1:
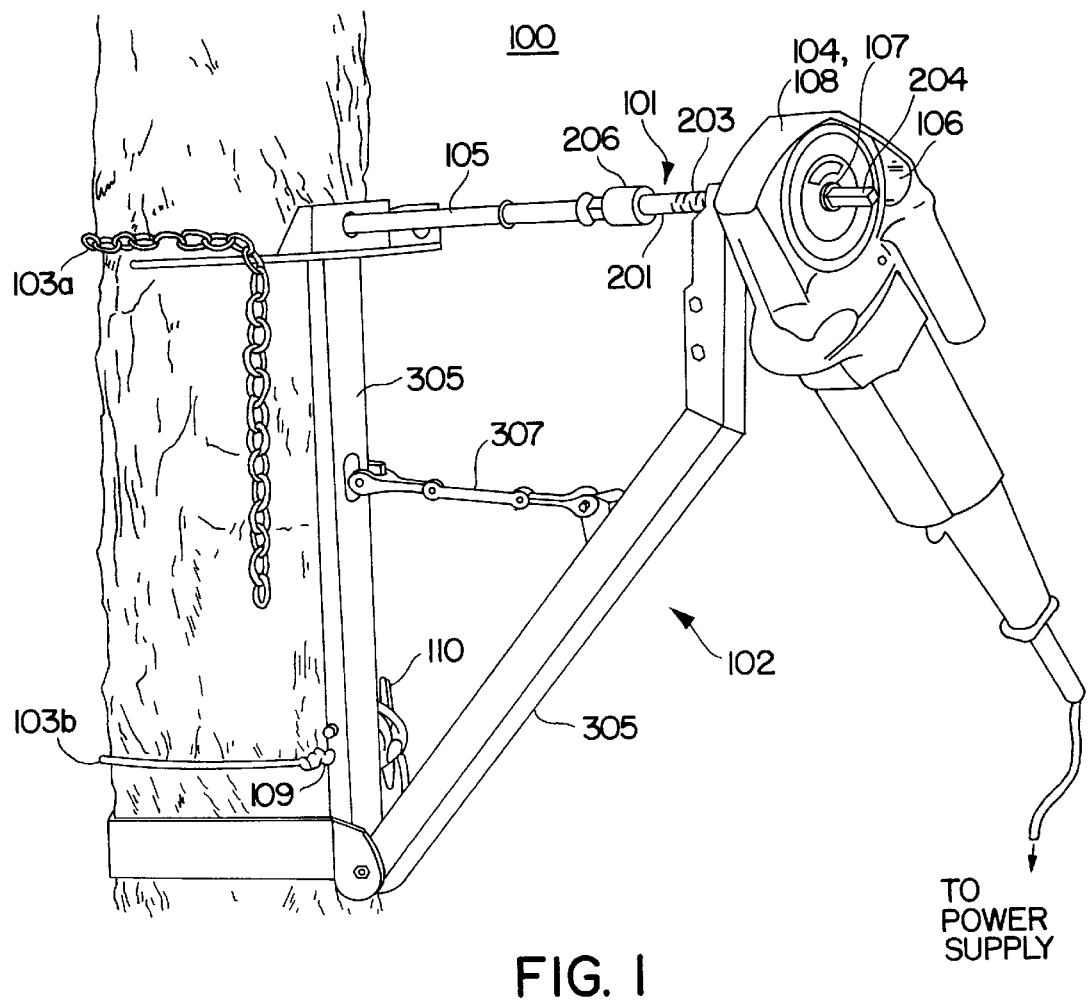
FIG. 1 shows a perspective view of a preferred embodiment of the system mounted to a tree during the initial drilling phase.

Referring to the drawings, a preferred embodiment of the boring system of the present invention is depicted. FIG. 1 shows a perspective view of the system mounted on an object, in this case, a tree. It should be noted that although a tree is depicted, the system is suitable for boring other objects such as, for example, telephone poles, treated timbers, structural supports comprising wood, concrete, or metal, and other objects in which there is a desire to bore holes and/or obtain core samples.

As shown, the system 100 comprises a frame 102 having a front and back orientation. The frame is depicted in FIG. 1 with its front against the tree. The system also comprises a drive assembly 101 which has a screw mechanism and is supported by the frame 102 during drilling. The drive assembly also may include rotating drive 104 for providing the rotating force. During drilling, the screw mechanism of the assembly 101 transfers a rotational force from the rotating drive 104 to a drill bit 105, and, at least initially, provides a forward axial force to the drill bit 105. The frame is held rigidly to the object by fastener 103. Each component of this system is discussed below in greater detail and in terms of preferred and alternative embodiments.

Figure 2:
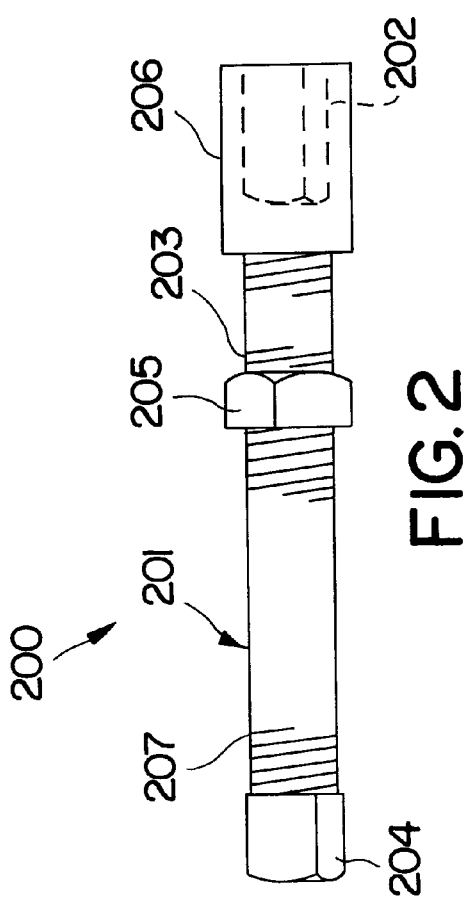
FIG. 2 shows a preferred embodiment of the driving assembly.

Referring to FIG. 2, a preferred embodiment of the screw mechanism 200 of drive assembly 101 is shown. The screw mechanism 200 comprises an elongated member 201, adapted to engage a drill bit 105, and a cooperating member 205 in threaded engagement with the elongated member 201 such that the cooperating member 205 and the elongated member 201 form a screw mechanism.

The elongated member 201 comprises a shaft 207, at least a portion 203 of which is externally threaded. In this embodiment, one end of the shaft has a coupling adapted for receiving and rotationally engaging a drill bit. Suitable couplings for receiving and rotationally engaging a drill bit are well known in the art and include, for example, a socket which receives the drill bit, a chuck which is tightened about the drill bit, a male portion which interengages with a corresponding female portion of a drill bit, or any other coupling known in the art for rotationally engaging two members.

Preferably, the coupling allows for unencumbered forward motion of the drill bit. More specifically, the drive assembly should engage the bit either directly or indirectly such that there is tolerance for the drill bit to move forward independently from the screw mechanism. Configurations of means for receiving and rotationally engaging a drill bi that allow for unencumbered forward axial movement include, for example, a socket, keyed shaft, or spline. As shown in FIG. 2, the coupling comprises a socket 206 which is secured on to an end 202 of the shaft 207.

The elongated member also comprises an interconnection to the rotating drive. Suitable interconnections to rotating drive are known in the art and include, for example, a nut, square shank, notch, slot and key, textured surface, or any other configuration or mechanism that provides a purchase point for a rotating drive. As shown, the interconnection comprises a square end 204 which is adapted to fit within an orifice 107 (FIG. 1) of the rotating drive 104.

The cooperating member 205 has threads adapted for interengagement with at least a portion of the cylinder member's threaded portion 203. When the threads of the elongated member and the cooperating member are interengaged, a rotational movement of the elongated member relative to the cooperating member results in their relative axial movement. The cooperation means may be any surface having threads, ridges, or groves, that sufficiently interengages with the threads of the elongated member to resist the axial forces between the cooperating member and the elongated member as they rotate relative to one another. Suitable cooperating members include, for example, nuts of all shapes and sizes, a threaded trough, notch or arcuate groove, and a hinged threaded clasp that clamps around the elongated member. Additionally, the cooperating member may be a discrete component, such as a nut, or it may be integral to or mounted on the frame. As shown, the cooperating member comprises a square nut 205.

In a preferred embodiment, the drill bit is threaded and the threaded portion 203 of the shaft 207 and the nut 205 have a lower pitch (for example, 12 threads per inch) than the drill bit (for example, 5 threads per inch). This way, once the drill bit bites the object being drilled, the drill bit will advance further per revolution than the elongated member. This differential in screw rates relieves the compressive forces between the frame, elongated member 201 and the drill bit. Once this force is relieved, the elongated member may be removed, and the rotating drive may be applied directly to the drill bit (discussed below).

In this embodiment, the length of the shaft 207 depends somewhat on the length of the drill bit. That is, the length of the drill bit and the shaft 207 up to the interengagement of the nut 205 should be substantially equal to the distance between supports that support the combination of the screw mechanism and drill bit during drilling. Since the frame support dimensions typically are not adjustable significantly, when using a shorter bit, a longer shaft 207 may be used or the engagement region between the nut 205 and the threaded portion 203 of the shaft 207 may be moved back to effectively lengthen the drill bit/elongated member combination.

Figure 1A:
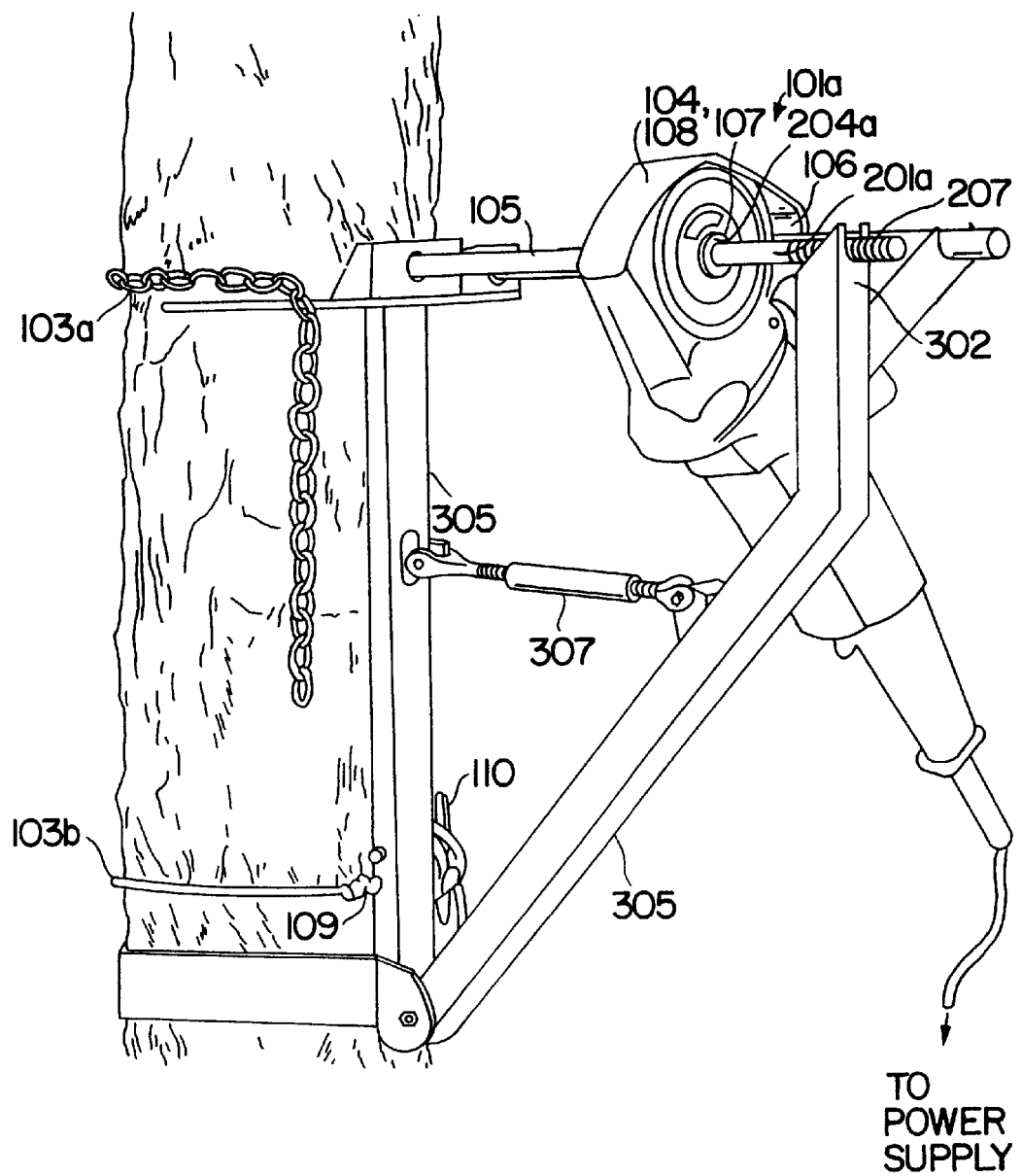
FIG. 1A shows a perspective view of another preferred embodiment of the system mounted to a tree during the initial drilling phase.

Another preferred embodiment of the drive assembly 101a is shown in FIG. 1a. This drive assembly is preferable for use with shorter drill bits. It is similar to the drive assembly 101, however, rather than the screw mechanism interengaging directly with a drill bit, the screw mechanism is operatively connected to the bit through the rotating drive 104. In other words, the rotating drive 104 serves to couple the screw mechanism to the drill bit.

Figure 2A:
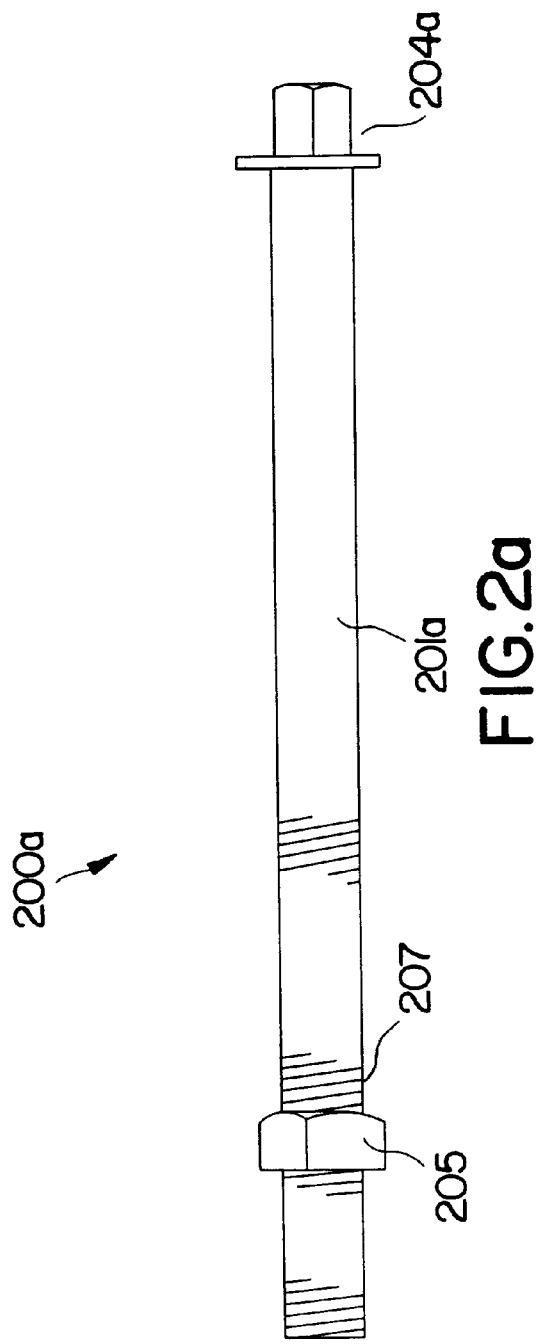
FIG. 2A shows another preferred embodiment of the driving assembly.

Referring to FIG. 2a, a preferred embodiment of the screw mechanism 200a of drive assembly 101a is shown. The screw mechanism comprises an elongated member 201a adapted at one end 204a to engage the rotating drive, and, as described above, a cooperating member 205 in threaded engagement with the elongated member 201a. The cooperating member 205 and elongated member 201a cooperate in manner similar to that as described above with respect to the screw mechanism 200.

The rotating drive of the present invention may be part of the drive assembly or it may be supplied separately. The rotating drive should be capable of delivering enough torque to the bit and/or the elongated member and bit combination to drill the object to the desired depth. Additionally, in many applications, it is preferable that the drill bit not rotate so fast such that it generates excessive heat which may damage the object, spoil the core sample, or damage the drill bit. In the case of forestry, the torques encountered range from about 50 lb. ft. to about 100 lb. ft., and a full load RPM of about 20 to about 30 is generally preferred. Thus, suitable rotating drives should be able to provide these torques at the desired RPM. Suitable rotating drives include, for example, electric, hydraulic and pneumatic systems, such as a drill, pipe threader or impact wrench, and manual means having mechanical advantages such as a crank, winch or T-handle.

Because core sampling or other drilling activity often is performed in remote areas, it is preferable that the rotating drive be powered by a convenient and transportable power source. Although hydraulic units provide the power and control required, the complexity and weight of such apparatus is often inconvenient or impractical. Therefore, in a preferred embodiment of the present invention, an electric motor is used for providing the required torque. Such a device can be conveniently powered by a portable 120V generator with ground fault protection suitable for outdoor use. The entire system, including the power supply, thus may be transported by a small all-terrain vehicle.

In the preferred embodiment, the rotating drive 104 comprises a conventional, hand-held, electrically-powered, pipe threading tool 107 as shown in FIG. 1. A suitable unit is the Model 600 pipe threading equipment offered by Rigid Tool (Elyria, Ohio). This unit has suitable speed and torque for the application, and is reversible. To releasably engage both the drill bit and the elongated member, it may be necessary to modify slightly the spindle of the pipe threading device. For example, the modification may entail cutting away the jaws from a ¾" pipe die head, reaming it to the outer diameter of an $^{11}/_{16}$" eight-point impact socket, inserting the socket half its length into the die, and welding it in place. The sockets may also require minor internal enlargement with a die grinder to properly fit the metric square drive of the core bit. Such a modification, or similar modifications, however, are well within the purview of one skilled in the art.

The drill bit also may be part of the system or supplied separately. Suitable drill bits include, for example, conventional, commercially-available drills, augers or other types of boring apparatus. These bits may be threaded or non-threaded. In forestry, for example, it is common to extract core samples for analysis purposes using a hollow, threaded boring bit 106 shown in FIG. 5. Such boring bits are commercially available, for example, from Suunto and Haglof (Sweden).

Figure 3:
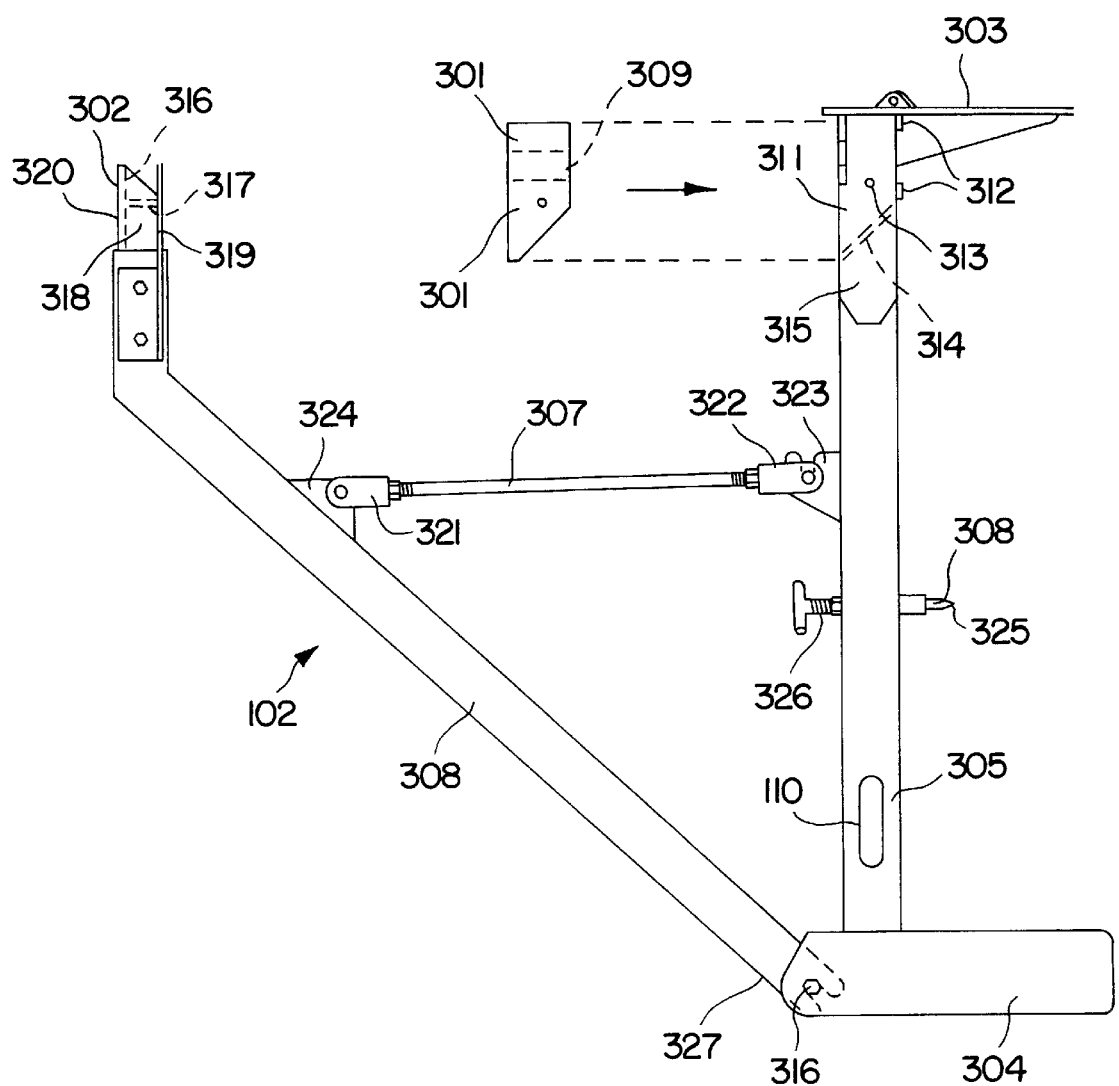
FIG. 3 shows a preferred embodiment of the frame.

As shown in FIG. 1, when drilling, the drive assembly 101 is supported by a frame 102 having a front and back orientation and at least one configuration, the "drilling configuration." The frame 102 not only supports the drive assembly and drill bit, but also guides the bit and provides a backstop against which the screw mechanism can urge forward. To this end, a preferred embodiment of the frame comprises first and second supports, 301, 302, as shown in FIG. 3 in its drilling configuration. It should be noted that the frame depicted in FIG. 3 differs slightly from the one shown in FIG. 1 in that the first support 301 does not project upward from the frame 102. Rather, the first support 301 is contained within the frame. This embodiment is preferred to avoid interference between the first support and the object being drilled when the frame is pivoted during mounting (discussed below).

The first support functions to support the drill bit at a point close to the object being drilled and to limit the lateral movement of the bit. Suitable support configurations include, for example, an orifice, trough, groove, clasp, bearing (roller, sleeve or ball), bushing or similar device to guide and support a drill bit. As shown in FIG. 3, the first support 301 has an orifice 309 which is adapted to receive a drill bit.

The first support preferably is made of a material softer than that of the bit such that it does not dull or in any way damage the bit. Suitable materials include, for example, wood, plastic, hard rubber, a polymeric composition, or a soft metal such as sintered bronze. In the preferred embodiment, the first support is wood due to its low cost and high configurability.

The first support may be threaded to cooperate with the drill bit or it may be non-threaded. Since drill bits may vary in thread pitch or have no threads at all, it is preferable to use a non-threaded first support. The first support should be as far forward as possible on the frame to maximize the length of the drill bit available for penetration into the object.

In the preferred embodiment, the first support 301 is removable from the frame. As shown in FIG. 3, the first supporter 301 has a trapezoidal cross section as viewed from the side. This shape allows the first support to be removed in the event that the drill bit cannot be reversed out or otherwise be removed from the object. The significance of the shape is discussed in more detail below in regard to the process of drilling.

In the preferred embodiment depicted in FIG. 3, the second support 302 is disposed behind the first support when the frame is in its drilling configuration. During drilling, the second support 302 supports the screw mechanism, which is either interengaged with the drill bit or operatively connected to the bit through the rotating drive or other coupling. (As described above, the other end of the bit is supported by the first support means). By supporting the screw mechanism, the second support 302 also aligns the drill bit/screw mechanism with the first support 301. The second support, at least during the initial drilling phase, resists the backward force of the screw mechanism. This involves holding the cooperating member from moving backwards or rotating as the combination of the elongated member and the interengaged drill bit are rotated. It is highly preferable for the second support to be configured such that the screw mechanism can be removed from the frame once the bit bites and advances forward through its own rotational movement. To this end, suitable configurations for the second support include, for example, a notch, vice, clasp or clamp adapted to receive the cooperating member.

Figure 3A:
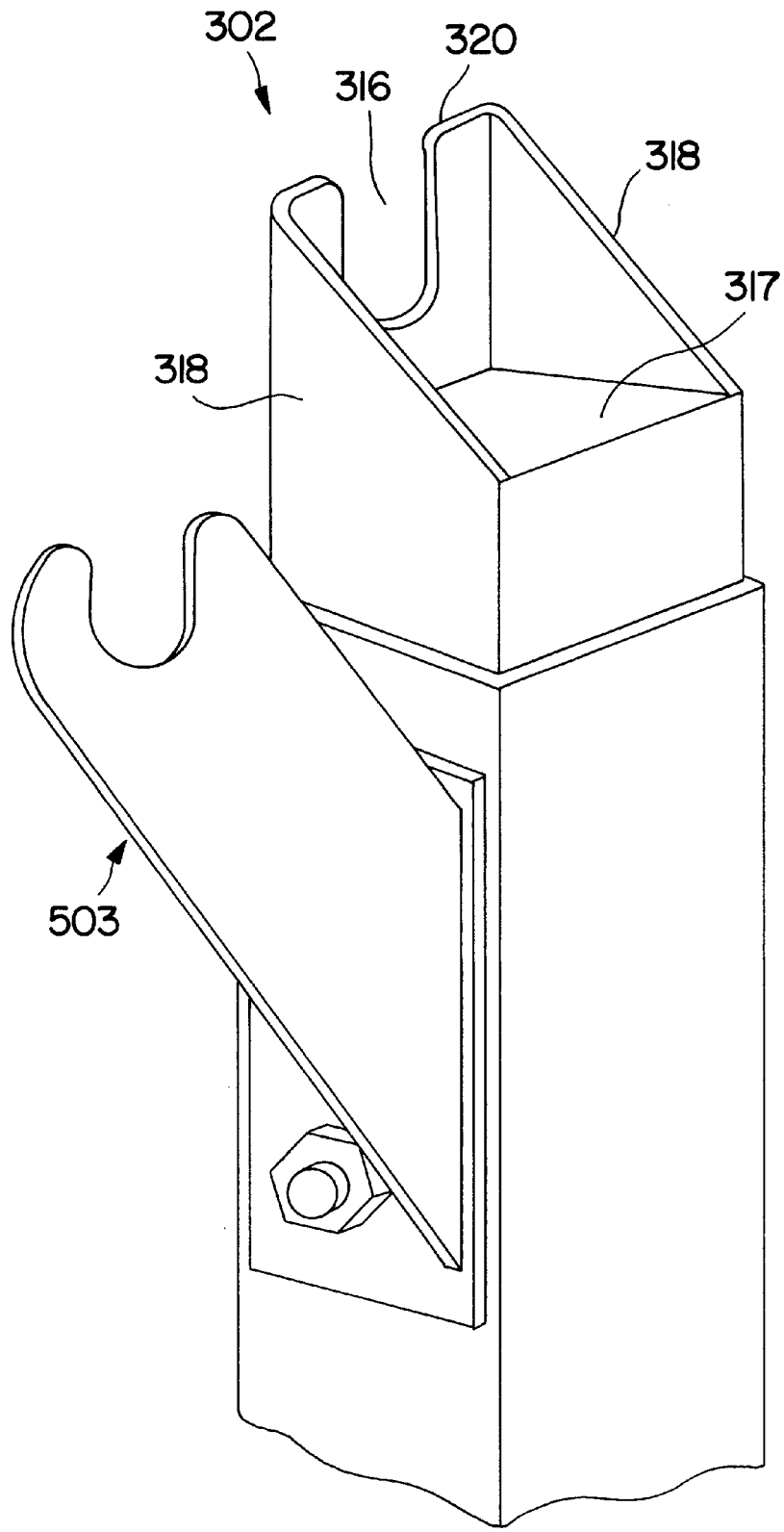
FIG. 3A shows a preferred embodiment of the second support of the frame of FIG. 3.

As shown in FIG. 3a, the preferred embodiment of the second support 302 has parallel side plates 318 and a rear plate 320. The rear plate 320 is slotted to accommodate and support the elongated member. In this embodiment, a vertical slot 316 allows the elongated member to be dropped into the second support 302 before drilling and readily removed once the bit bites. Rather than a vertical slot, the slot or notch have a diagonal or zig-zag configuration depending upon the needs of the application. A shelf 317 is provided for supporting the cooperating means, in this embodiment, a nut 205 (See FIG. 2). The side plates 318 are spaced apart such that the nut cannot rotate when seated on shelf 317. Additionally, the rear plate 320 is sufficiently strong to resist the axial force exerted by the nut as the cylindrical means is rotated. In this way, the rear plate 320 of the second support acts as a backstop for the screw mechanism.

In an alternative embodiment, the second support may be integral with the cooperating member. That is, the second support may have threads, ridges or grooves for interengaging the threads of the elongated member. Such a configuration may include, for example, a section of the frame having a threaded orifice.

In a preferred embodiment, the first and second supports are adjustable, up and down and/or side to side. This feature allows the drill bit/drive assembly to be adjusted and "aimed" before drilling the object. Such adjustment capability may be achieved, for example, by tolerance in cavity 311 containing the first support 301, thereby accommodating limited movement of the first support 301 within the cavity. Other means of adjustment may include set screws, on one or more sides of the first support, to move the first support accordingly and/or to hold it in its adjusted position. The second support may be adjustable by altering the position of the first and second members relative to each other with, for example, a brace 307 as described below.

The frame may also comprise one or more mounts for interfacing with the object when drilling. Suitable means depend somewhat on the contour of the object to be drilled. For example, if the object is relatively planar, the mount would be relatively planar. On the other hand, if the object is cylindrical or spherical, then the mount should have a concave profile.

Figure 4:
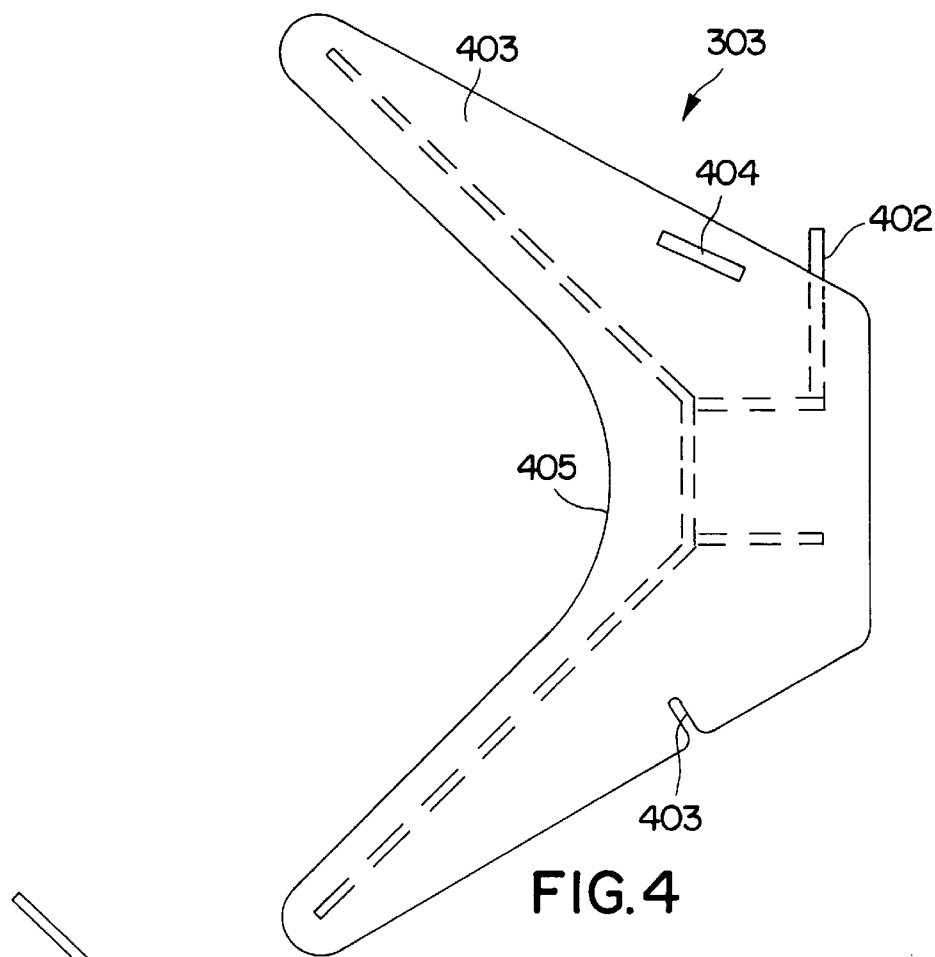
FIG. 4 shows a preferred embodiment of a first mount of the frame of FIG. 3 and the first mount's interaction with the upper fastener.
Figure 5:
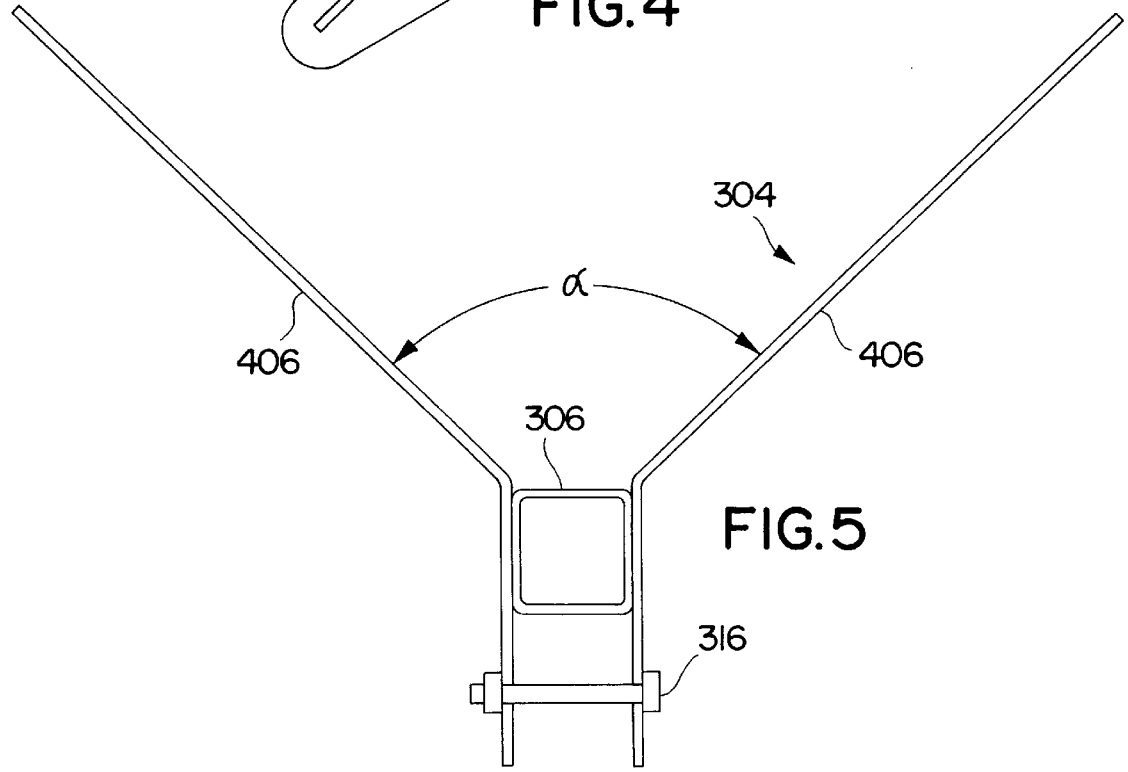
FIG. 5 shows a preferred embodiment of a second mount of the frame of FIG. 3.

FIG. 3 shows a preferred embodiment of the mounts. As shown, the frame comprises first and second mounts 303 and 304, respectively. The first mount 303 is a plate disposed proximate to the first support 301, while the second mount 304 is a predetermined distance from the first mount 303. As shown in FIG. 4, the leading edge 405 of the plate of the first mount is concave or forked to receive a cylindrical or conical object. In FIG. 5, a preferred embodiment of the second mount is shown. Unlike the first mount, the second mount comprises two plates 406 that are connected on their planar surface (perpendicular to the drawing) to the frame at an angle α to one another. This angle, like the concave edge of the first mount, is adapted to receive a cylindrical or conical object like a tree.

The general shape of the frame can vary providing that it supports the drive assembly and drill bit and can be rigidly secured to a tree. For example, it may have a triangular, square, or other profile; it may be cast or a structure of tubular or rectilinear sections; or it may be integral or comprised of discrete interconnecting components. In the preferred embodiment of the frame shown in FIG. 3., the frame is a structure of discrete, releasably-engaged components to provide a combination of structural strength, light weight and convenience. This design allows for not only a drilling configuration, but also a collapsed configuration for easy transportation and handling.

As shown, the frame has rectilinear first and second members 305, 306, respectively. These members may be comprised of steel tube, angle iron, or other rigid, strong material. The first and second mounts 303, 304 are disposed at proximate opposite ends of the first member 305. The second member 306 is pivotally and releasably engaged at end 327 to the second mount 304. Being pivotally and releasably connected allows the second member 306 to be angled to the first member 305 in the frame's drilling configuration, or to be dismantled or folded up closely to the first member 305 in a collapsed configuration (not shown).

When in the drilling configuration, the brace 307 extends between the first and second members 305 and 306 and holds them rigidly at an angle to one another. The brace should be designed to withstand high tension loads. Suitable braces include, for example, cable, chain, rods, and turnbuckles. Preferably, the brace not only provides tension resistance, but also serves to rigidly hold members 305 and 306 together. As such, turn buckles, rods, and other stiff members are preferred. As shown in FIG. 3, the brace 307 is a rod having adjustable shackles 321 and 322. The shackle 321 pivots on a mount 324 on the second member 306 and the other shackle 322 cooperates with a notched mount 323 on first member 305 for releasable engagement.

In this preferred embodiment, the first support 301 is disposed along said first member 305 at a certain distance away from where the fastener connects to the first member 305. More specifically, the first support 301 is below the first mount 303, which, as discussed below, is the point at which the upper fastener connects to the frame. By spacing the upper fastener from the first support, the chance of the drill bit exiting the far side of the object during drilling and being damaged by or damaging the fastener is reduced.

Figure 7:
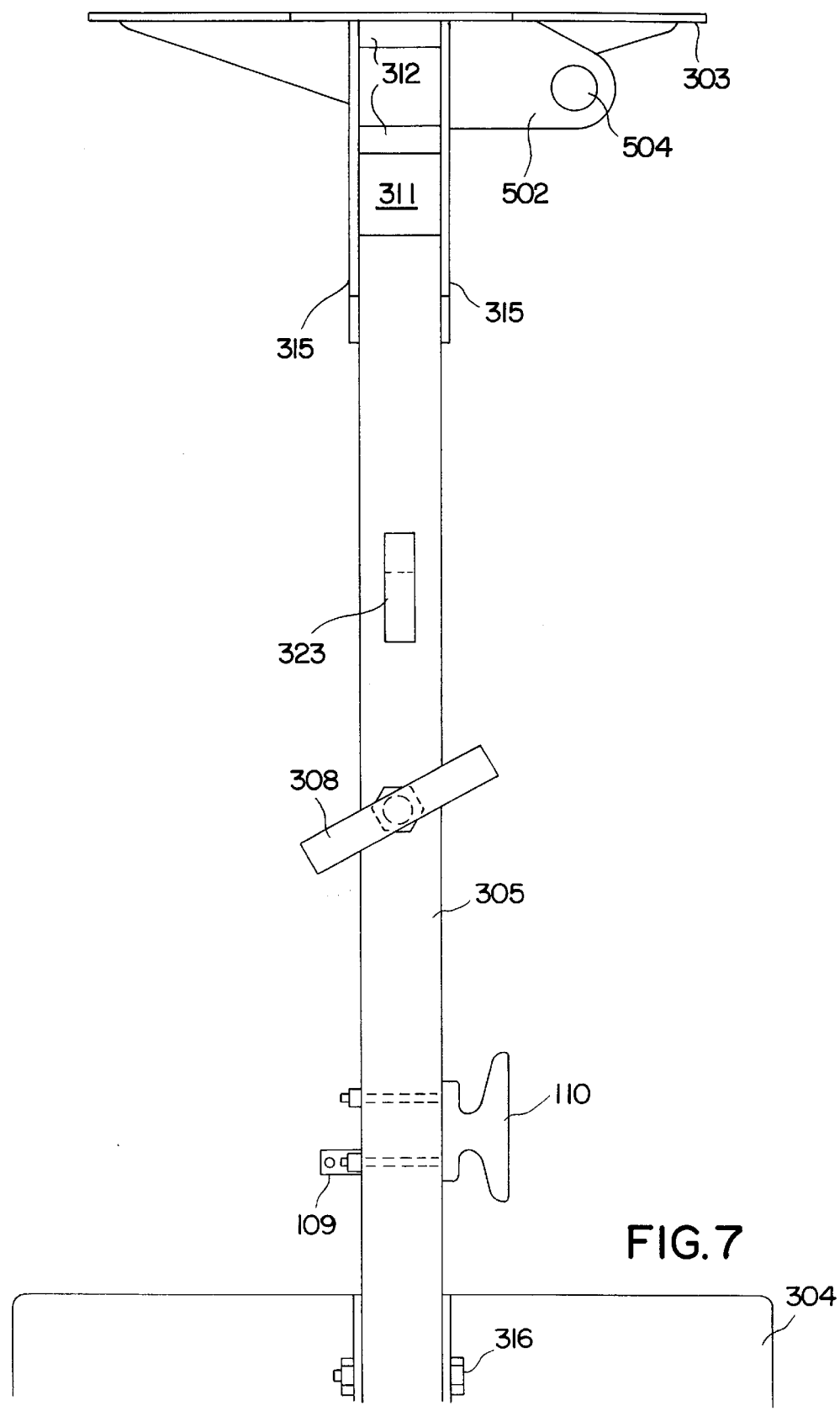
FIG. 7 shows a back view of the first member of the frame of FIG. 3.

In the preferred embodiment, as shown in FIGS. 3 and 7, a cavity 311 for the first support 301 is created by connecting the first mount 303 to the first member 305 with flat bars 315. Within the cavity, the first support is held in by two horizontal backing bars 312 and a push pin 313 with spring loaded retainer (not shown). The bottom 314 of this cavity 311 is sloped downward from front to back. This slope accommodates the drill bit when the first support 301 is removed and the frame is pivoted upwards to remove the frame when the drill bit cannot be reversed out (discussed below).

Figure 6:
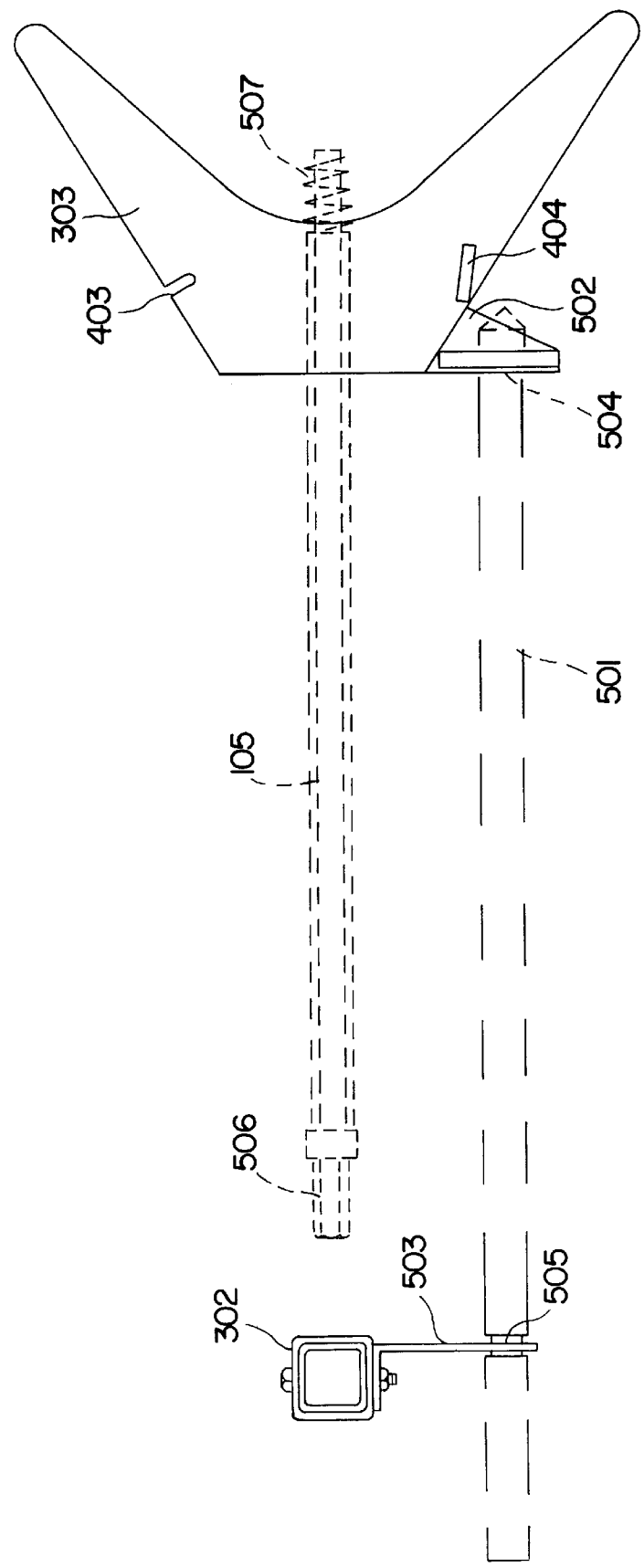
FIG. 6 shows a top view of a frame of FIG. 3 with the rigid rod indicated as a phantom line.

When encountering high torque, it may be beneficial to prevent the rotating drive from counter-rotating by using torsional-resistance mechanism. Many variations of the torsional-resistance mechanism will be apparent to those skilled in the art. The torsional-resistance mechanism may be any mechanism which holds the rotational means from rotating relative to the frame. Suitable mechanism include, for example, a bar, strap, hook or other such means for hindering the counter-rotation of the rotating drive. In the preferred embodiment, as shown in FIGS. 6 and 7, the frame has rod mounts 502 and 503 with orifices 504 and 505, respectively, for receiving a rigid rod 501. When the frame is in its drilling configuration, the rigid rod 501 extends from front to back substantially parallel to the drill bit and/or the combination of the drill bit and drive assembly. Rigid rod 501 provides a surface which the rotating drive can urge against. In a more preferred embodiment in which the rotating drive is a pipe threader, the rigid rod 501 has a cross sectional profile suitable for insertion through an orifice 106 of the pipe threader (see FIG. 1). This way, as the pipe threader spins the drill bit, and the drill bit advances into the object being drilled, the threading device slides axially along the rigid rod.

The frame is held rigidly to the object to be drilled by one or more fasteners. Suitable fasteners include any conventional device or devices used to secure one object to another, such as, for example, devices that wrap around the object such as chains, straps, lines or cables as well as devices that mechanically engage the object such as spikes, screws or other types of fastener. In a preferred embodiment, two or more fasteners are employed. It is also preferred that the fasteners, particularly those that wrap around the object, tighten easily. This tightening action may be accomplished in a variety of ways, including, for example, by leveraging off the first support (described below), or by traditional tie down or tensioning mechanisms, for example, a chain fall, block and tackle, or strap lever.

The preferred embodiment shown in FIG. 1 has upper and lower fasteners, 103a and 103b, respectively, for securing the frame to the object. The top fastener 103a is a chain and the lower fastener 103b is a non-stretching cord. FIG. 4 shows one preferred embodiment of the interaction between the first mount and the upper fastener. As shown in this figure, a pad eye 404 is adapted to receive a link of chain. This chain can be wrapped around the object and brought back and secured in slot 403. As shown in FIG. 1, the lower fastener 103b can be fastened to the frame at point 109, wrapped around the object and cleated to the frame on cleat 110.

In the embodiment shown in FIG. 3, an additional fastener, a tree spike 308, is affixed to the frame. It has been found that some species of trees require this feature. For example, during coring dense wood and large trees, the power tool reaction on the frame, which is principally downward, increases. At times, the frame may slip down slightly so the first support 301 is bearing on the top of the core bit. The tree spike is intended to augment the tree clamping capability and prevent slippage. A first support of anti-friction material such as ultra high molecular weight polyethylene also improves this situation. The tree spike 308 shown in FIG. 3 is a T-shaped member having a pointed end 325 and a threaded shaft 326 that cooperates with the first member 305. By rotating the T-shaped member, the tree spike 308 moves axially such that it may be screwed into the tree prior to coring. Although a T-shaped member is shown in FIG. 3, other embodiments, such as screws or nails may be used.

The operation of the above-mentioned system is straightforward and easily conducted in remote areas. In a preferred embodiment, the method comprises the steps of: (a) mounting the frame to the tree using the fasteners; (b) engaging the drill bit with the screw mechanism; (c) engaging the screw mechanism with the frame; and (d) rotating the screw mechanism. During the initial drill phase, when the screw mechanism is operatively engaged with the drill bit and rigidly supported by the frame, a clockwise rotation of the mechanism (in the case of right-handed threads) will result not only in the drill bit rotating, but also in its forward advancement due to the screw action of the screw mechanism. The forward advancement urges the drill bit into the object. As mentioned above, it may be advantageous to remove the screw mechanism if and when the bit "bites."

By way of example, the method will be described in regard to the preferred embodiment of the frame 102, shown in FIG. 3, taking a tree core sample. First, the frame 102 is rigidly fastened to the tree, with the first support 301 being positioned at the desired location for taking the core. This is done by placing the first mount 303 against the tree, tilting the first member 305 up at an angle to the tree, preferably about 45 degrees, passing the upper fastener 130a (shown in FIG. 1 as chain) around the tree, and fastening it loosely. The lower end of the first member 305 is then pushed downward, pivoting the first member on the first mount until the second mount meets the tree. This motion tensions the upper fastener by leveraging off the "forked" geometry of the first mount 303 (see FIG. 4). The upper fastener 103a should be adjusted such that the first mount 303 bites firmly into the tree just as the second mount 304 contacts the tree. The lower fastener 103b (shown in FIG. 1 as a cord) is then passed around the tree and cleated. These steps result in the first member 305 being rigidly mounted to the tree.

Once the first member 305 is rigidly secured to the tree, a slotted end 327 of the second member 306 is positioned on the pivot pin 316, at the bottom of the frame. Next, the brace 307 is hooked between the first and second members 305 and 306. The length of the brace 307 is configured such that the first and second supports 303, 304 are aligned in regard to the desired direction of the drill bit. These steps result in the complete frame being prepared to receive the drill bit and screw mechanism.

The geometry of the mount, particularly the forked or concaved profiles of the first and second mounts, receives the curved surface of the tree such that the screw mechanism aligns with the center of the tree. The driving end 506 of the drill bit 106 (FIG. 6) is inserted in the socket 202 of the elongated member 201 (FIG. 2). The bit is then inserted through the first support 301, and the threaded portion 203 of the elongated member 201 together with the cooperating member 205 (FIG. 2) is entered into the slot 316 of the second support 302. The cooperating member 205, in this embodiment, a free-running square nut, is prevented from rotating by the side plates 318 and the shelf 317. At this point, the screw mechanism is fully supported by the frame.

Before drilling, a user can sight down the drill bit and screw mechanism to check the drill bit's direction. If adjustment is necessary, then the user may move the first support and/or the second support to achieve the desired entry into the tree.

Once the user is satisfied with the aim of the drill bit, the drill bit and screw mechanism are rotated freely by hand until the elongated member pushes the bit firmly against the tree. At this point, the screw mechanism is prepared to force the core bit 105 into the tree.

The rotating drive is engaged with the screw mechanism, and rotation begins in a clockwise direction. For the first inch or so, the elongated member 201, being in threaded engagement with the cooperating member and effectively the frame, advances and crowds the bit into the tree with increasing force. Eventually, the bit "bites" or engages the tree. Since the bit threads have a coarser pitch than those of the cooperating member/elongated member, the drill bit begins to advance faster than the elongated member per turn. At some point, the elongated member becomes free and can be easily removed. Alternatively, a drill bit may have no threads, in which case, the screw mechanism is kept in place to provide the forward urging force. The rotating drive may be engaged directly to the bit if the screw mechanism is removed. It may be preferable to wrap a rubber band, tape or other type of marker around the drill bit as a depth gauge so that the user can easily determine when the proper length of bit has been drilled into the tree or object being drilled.

To guide the drill bit and prevent the rotating drive from counter-rotating, a rigid rod is secured to the frame by inserting it through orifices 504 and 505. The rotating drive can then urge against the rod to prevent its counter rotation. In the preferred embodiment shown in FIG. 1, the rotating drive has an orifice 106 for receiving the rigid rod. Holding the rotating power tool firmly, and using the rigid rod to control the tool's reaction, the bit may be fully drilled through the tree.

An alternative method of drilling using shorter bits is shown in FIG. 1a. In this arrangement, the rigid rod 501 is inserted through the orifice 106 of the pipe threader 108 and mounted to the frame. The drill bit is inserted through the front support 301 and interengaged with the pipe threader 108. Next, the screw mechanism 201a of the drive assembly 101a is interengaged with the pipe threader. The cooperating member, which in this embodiment is a square nut, is then adjusted to slightly forward of the rear plate 320 (FIG. 3a) is dropped in the second support 302.

At this point, the boring system is ready to begin drilling. To this end, rotation is commenced while maintaining alignment between the bit, screw mechanism, and expected tree center. When the bit bites and it advances forward as a function of its own rotational movement, it will tend to move forward faster than the screw mechanism. Hence, the need for axial tolerance between the screw mechanism and the drill bit. Once the drill bit moves away from the screw mechanism, the mechanism can be removed while drilling continues.

Once the drilling phase is complete, a core is extracted from the core bit. This extraction may be performed using a conventional extractor and conventional techniques. In the preferred embodiment, however, the drill bit is drilled just through the tree such that the end of the drill bit can be tapped with a block to break the core free from the tree. Once the core is severed from the tree, the core can be pushed out of the drill bit using a dowel or similar tool. After the core is extracted, the bit is backed out and removed. Alternatively, the core can be removed from the drill bit after the drill bit is removed from the tree.

Once the drill bit is removed, the frame is removed in the opposite sequence from installation. More specifically, the lower fastener 103b is uncleated. Then, the lower end of the first member 305 is lifted upward, pivoting the first member on the first mount until the first member is at about a 45 degree angle with the tree. This motion loosens the upper fastener. Finally, the upper fastener 103a is unfastened and the frame removed.

It should be noted that setting up the frame and drilling the object can be separated into two distinct steps in this process. Moreover, the rotating drive and the frame are physically independent of one another. Consequently, while the rotating drive is being used to drill one tree, one or more other frames may be mounted and readied for the rotating driver. This improves efficiency since setting up the frame often is very time consuming.

When drilling, a hollow or soft spot may be encountered, wherein the drill bit can no longer bite, and consequently cannot be advanced or reversed. In such a situation, the first support 301 can be removed thereby allowing the frame to be tilted for removal just as it was installed. In such situations, it is common for the bit to be removed by cutting the tree and splitting the core section. The present invention, however, also provides for a system for extracting the lodged drill bit without sacrificing the tree.

Figure 8:
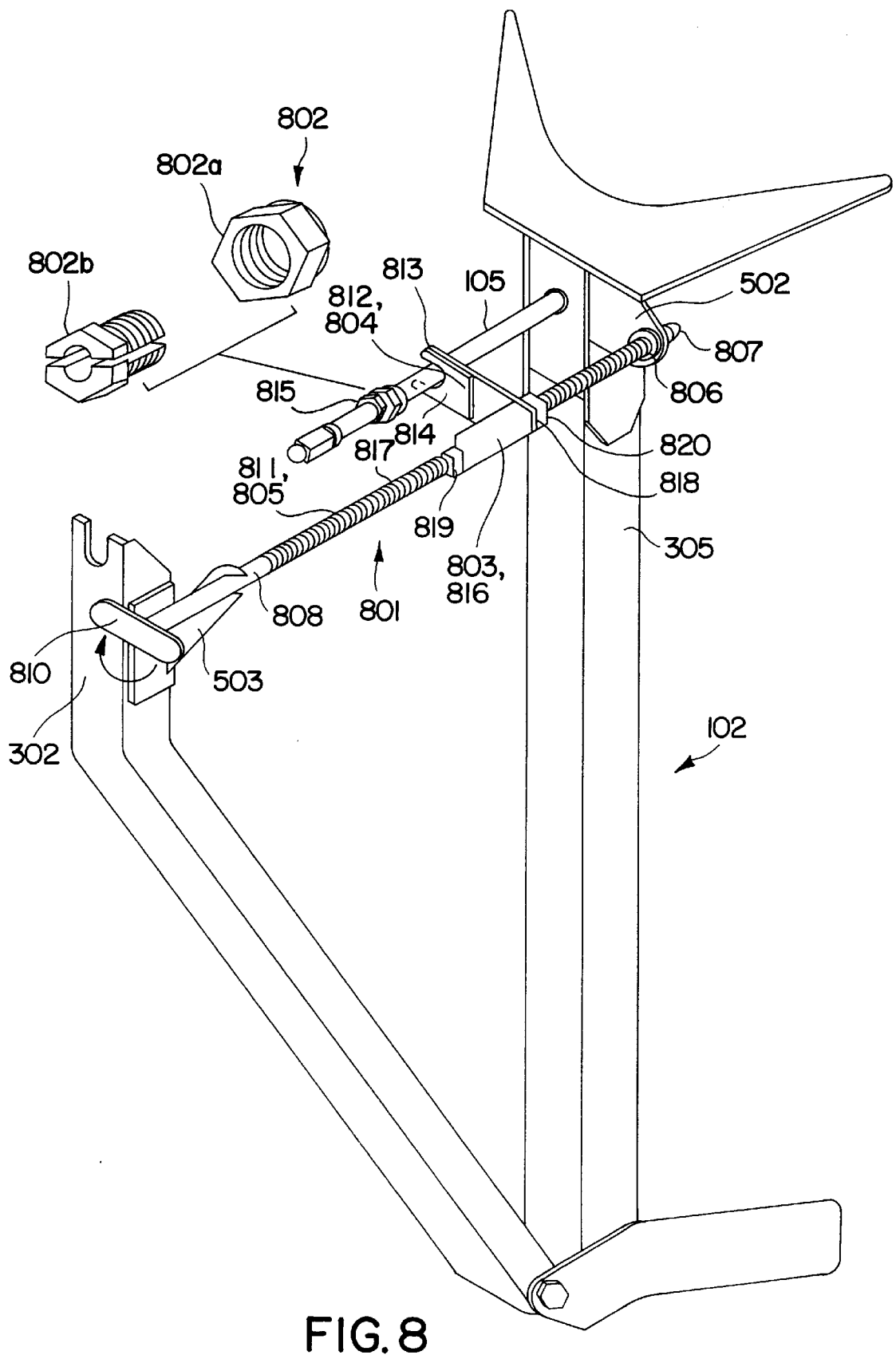
FIG. 8 shows a perspective view of a preferred embodiment of the extracting system.

FIG. 8 shows a preferred embodiment of the extractor of the present invention. The extractor comprises a frame 102 (as described above), fasteners for securing the frame 102 to the object being drilled (not shown, but the same as described above), and extractor assembly 801 configured to provide a backwards urging force against the drill bit 105 or structure associated with the bit.

The function of the extractor assembly 801 is to provide a backwards urging force against drill bit 105 such that when bit 105 is rotated in reverse of its drilling direction, it has the tendency to back out. Preferably, the extractor assembly is a screw mechanism comprising an elongated first component and a second component in threaded engagement with the first component such that rotating the first component relative to the second component results in the relative axial movement of the second component relative to the first component. Either the first or the second component is configured to contact or engage the drill bit to urge it backward.

FIG. 8 shows a preferred embodiment of the extractor assembly comprising a screw mechanism parallel to the drill bit. As shown, the screw mechanism comprises a first component 805, rotatably mountable to frame 102, and a second component 803, which is configured for screw engagement with first component 805 such that rotation of the first component 805 results in axial movement of second component 804. The second component is configured to contact the drill bit through the screw action of the first and second components.

In this particular embodiment, the first component 805 is a lead screw 811 having a threaded portion 817 and non-threaded, portions 808 on either side the threaded portion. The non-threaded portions provide a bearing surface that renders the first component suitable for rotational mounting on the frame 102. In the preferred embodiment, the lead screw 811 mounts to the frame in the same location as the counter-rotation member mounts to the frame. More specifically, the first component is supported at its front end by the first rod mount 502 and at its back end by the second rod mount 503. The more preferred embodiment of the invention also employs an anti-friction thrust bearing 806 with a bearing guide 807 at the first rod mount.

The first component is configured to be rotatable, and, as such, preferably has a handle 810 to facilitate rotation. Other means of rotating the first component, however, are within the scope of the present invention. For example, the first component 805 can be adapted for interengagement with the rotating drive 104 if desired.

The second component 803, as shown in FIG. 8, is a carriage assembly 816 having a threaded portion 818 for screw engagement with the lead screw 811 and an extension 804 for contacting drill bit 805 or its associated structure. In this embodiment, the threaded portion comprises two nuts, a front nut 820 and a back nut 819. The back nut 819 is split so that the carriage assembly does not bind on the lead screw 811. It will be obvious to those skilled in the art that the threaded portion may assume a variety of different embodiments, for example, it may comprise an elongated nut or internally-threaded bar stock.

The extension 804 in this embodiment is a fork 812 designed to accommodate the drill bit 105. More specifically, the tines 813 of the fork 812 are separated sufficiently to accommodate the drill bit 105 therebetween. The area around the tines accordingly is designed to contact structure radially extending from the drill bit. Although a forked extension is preferred, a variety of other configurations are possible within the scope of the invention. For example, the extension may comprise a hinged collar that clamps about the drill bit. The collar may have a bearing surface therein to facilitate the rotation of the drill bit.

Although the embodiment of the extractor assembly shown in FIG. 8 is preferred, other embodiments are possible within the scope of the invention. For example, first and second components may be configured such that rotation of the second component results in the axial movement of the first component, which, in turn, is configured to act upon the drill bit. Moreover, rather than a parallel screw mechanism, the extractor assembly may be configured with an axial screw mechanism. The axial screw mechanism would be similar to that of the drive assembly, although instead of being configured to apply a forward urging force, the mechanism would be configured to apply a backward urging force. In the case of an axial screw mechanism, the rotating component of the screw mechanism interengages with the drill bit using conventional means, such as, for example, a coupling, a clasping mechanism that clasps around the drill bit, or a wheel pulling-type mechanism having fingers that engage the drill bit and tighten as the mechanism is retracted from the drill bit.

If an axial screw-type mechanism is used, it is preferable that the interface between the bit and the screw mechanism accommodate some unencumbered backward axial movement of the drill bit. That is, since threaded drill bits typically are used, it is likely that at some point during the process of extracting a bit, the threads of the bit will bite and the bit will begin to back out without urging. In fact, the bit will tend to move backward more per revolution than the screw mechanism since the threads of the bit generally have a higher pitch. Without some tolerance for a difference in axial travel rates, the drill bit will tend to urge against the screw mechanism and bind.

As shown in FIG. 8, a preferred embodiment comprises a structure associated with the drill bit to provide the bit with a radially extending surface which the extension 804 can contact. In this particular embodiment, the structure is a collar assembly 802 comprising a thrust bushing 802a which has an interior diameter which will slip over the drive end of the drill bit and has internal tapered threads to accept a two-piece collet 802b. Collet 802b has tapered common male threads to engage the thrust bushing 802a and is bored with an internal diameter suitable to clamp the bit shank. Such an assembly provides a strong surface against which the extractor assembly can urge against the drill bit 105. Although this collar configuration is preferred, other structures are possible within the scope of the invention. For example, rather than having a collet and bushing collar assembly, a hinged or two piece collar can be used that tightens to the shank of the drill bit with fasteners. Moreover, rather than urging against structure attached to the drill bit, the extractor assembly may urge against structure integral to the drill bit such as a lip 815 which is commonly machined on boring bits used in forestry. Furthermore, rather than urging against a surface extending radially from the drill bit, the extractor assembly simply may couple to the bit. Still other means of providing a contact point for the extractor assembly will be apparent to one skilled in the art.

Referring back to FIG. 8, since the extension 804 is configured to urge against collar assembly 802 while the drill bit 105 is being rotated, it is preferable to provide friction reduction means between the two components. To this end, an anti-friction shoe 814 comprised of a low friction material, such as TEFLON or high density polyurethane, may be disposed at the contacting surface of the extension component, or, alternatively, it may be disposed on the collar assembly. Other friction reducing means include, for example, conventional bearings or lubricants such as grease.

In a preferred embodiment, the extractor assembly also comprises a resilient member operatively disposed between the drill bit 105 and frame 102 and configured to urge the two apart when deformed. The resilient member preferably is deformed through the screw action of the first and second members against the drill bit.

Figure 9:
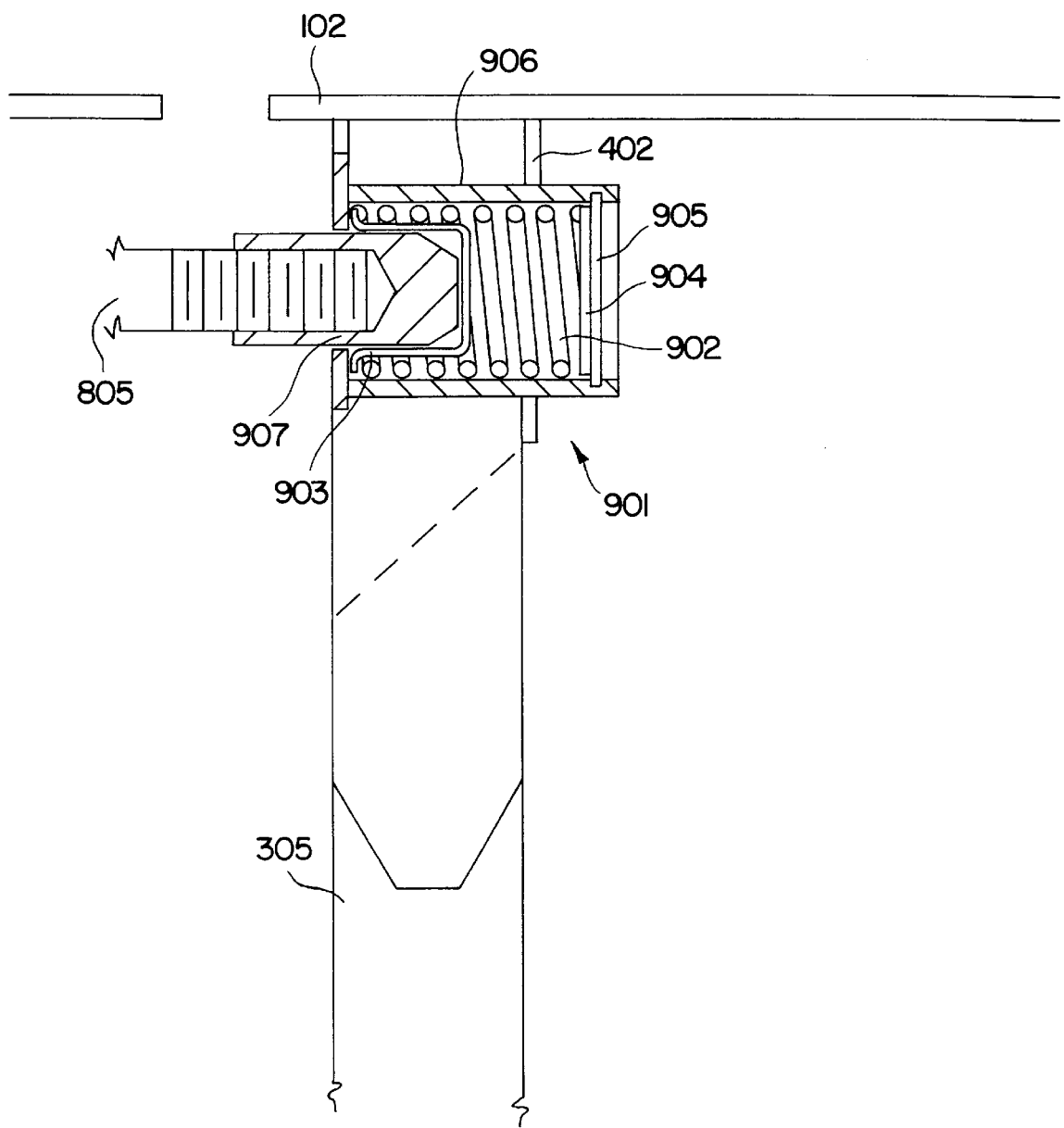
FIG. 9 shows a preferred embodiment of the resilient member.

A preferred embodiment of the resilient member is shown in FIG. 9. In this embodiment, a spring assembly 901 is disposed in the first rod mount 502 of the frame. More specifically, spring assembly 901 comprises a compression spring 902 contained within a housing 906 and held from moving forward by internal snap ring 905 which is secured to housing 906. A top hat-shaped member 903 is disposed in back of the spring and adapted to urge against the spring. The top hat-shaped member also is adapted for receiving a bearing surface 907 of first component 805. Preferably, the top hat-shaped member 903 is adapted to receive not only the first component 805, but also the rigid rod (described above). A backing plate 904 is disposed adjacent to the internal snap ring 905 and limits the forward travel of the top hat-shaped member 903.

The spring assembly is loaded by compressing it through the screw action of the lead screw and carriage assembly against a lodged bit. As described in greater detail below, when first component is moved forward as a reaction to the screwing force being exerted on the drill bit, spring 902 compresses. When compressed or loaded, the spring urges the first component 805 backwards.

Although the spring assembly described in FIG. 9 is preferred, other configurations are possible within the scope of the present invention providing that they ultimately provide a force urging the frame assembly 102 and the drill bit 105 apart. For example, rather than having a spring assembly with a top hat-shaped member 903, it may be preferred to have a spring disposed around the first component. By restricting the axial movement of one end of the spring and having the other end either connected to or urging against the frame, any forward axial movement of the first component caused by the screw action against the bit will cause a backward, resultant force in the spring.

Rather than disposing the resilient member between the first component and the frame, it may be preferable to place the member between the first and second components of the screw mechanism or between the screw mechanism and the drill bit itself. Regardless of the spring's location, the result of having the bit urged backwards from the frame is the same.

It should be understood too, that the resilient member can be means other than a spring. For example, the resilient member may be a flexible extension member 804 which is flexed forward against the collar assembly as the carriage moves backward. Once flexed, the extension member would apply a backwards force against the bit.

In operation, the extraction means of the present invention serves to provide a constant, backward urging force on the drill bit as it is reversed out of the tree. More specifically, once it is determined that a drill bit is stuck, and cannot be reversed out of the tree, the power drive tool and torque bar are removed from the drilling assembly. Next, the thrust bushing is placed over the core bit with the bearing surface toward the tree. In the embodiment involving a two-piece collar assembly as shown in FIG. 8, the two-piece collar assembly is tightened slightly and then slid back against the lip 815 of the drill bit and then hand tightened until it is snug. Once the collar assembly is secured to the drill bit, the first component, i.e., the lead screw, is inserted where the counter rotation bar previously engaged the frame. This is done typically by inserting first the front end of the lead screw into the top hat member 903 (FIG. 9) and then sliding the back end of the lead screw into the second rod mount 503 of the frame assembly. During the installation of the lead screw, it is advisable that the fork extension means be displaced about the drill bit 105.

At this point, the extraction process is ready to begin. Accordingly, the handle 810 of the lead screw 811 is rotated (as indicated by the arrow) such that carriage assembly 803 moves in a backward direction. Once the fork extension member 804 meets the collar assembly 802, the backward axial movement of the carriage assembly 803 will be resisted. This resistance is the backwards urging force on the drill bit that will facilitate its removal as the drill bit is rotated in reverse.

In one embodiment, during the extraction process, the bit 105 will be reversed while the lead screw is rotated. This is done until the bit threads re-engage or the bit is fully extracted.

In the preferred embodiment shown in FIG. 9 and described in the corresponding text, a resilient member is used to provide a backward urging force on the drill bit. If such resilient member is used, lead screw 811 is rotated past the point at which the carriage assembly meets the collar assembly. This way, the rotating force of the lead screw 811 against the immovable drill bit 105 will cause the lead screw 811 to move axially forward and compress the resilient member.

With the utilization of a resilient member, the drill bit need not be reversed simultaneously with the rotation of lead screw 811, since a backwards urging force can be "stored" in the extractor assembly through the resilient member. This allows the operator to turn the lead screw and store the energy and then back the drill bit out. Depending upon the situation, the operator may need to re-compress the resilient member periodically through the rotation of the lead screw 811 if the threads on the drill bit 105 do not engage within the length of the spring's compression.

What is claimed is:

1. An extractor system for removing a drill bit lodged within an object being drilled, said extractor comprising:
    a frame securable to an object and having a front and back orientation and being positionable in at least an extracting configuration; and
    an extractor assembly removably mountable to said frame and adapted to impart an urging force against a drill bit lodged within said object in a direction opposite the forward axial drilling direction of said drill bit to remove said drill bit from said object.

2. The extractor system of claim 1, wherein said extractor assembly comprises an extraction screw mechanism, said extractor assembly comprising:
    an elongated threaded first component removably mountable to said frame in said extracting configuration wherein said first component extends from front to back relative to said frame; and
    a threaded second component adapted for rotational engagement with said first component; and wherein said first and second components are configured such that rotating one of said first or second components in a particular direction causes the other component to move opposite the forward axial drilling direction and provide said urging force.

3. The extractor system of claim 2, wherein said extraction screw mechanism is positionable parallel to said drill bit, and wherein:

said first component is a lead screw; and said second component is a carriage assembly, said carriage assembly being configured for screw engagement with said lead screw, said carriage assembly having an extension extending radially with respect to said lead screw when engaged with said lead screw, said extension being adapted to transfer said urging force to said drill bit.

4. The extractor system of claim 3, further comprising:

a collar assembly securable to said drill bit and adapted to provide a contact surface extending radially from said drill bit for transfer of said force from said carriage assembly.

5. The extractor system of claim 4, wherein said extension comprises tines configured to accommodate said drill bit therebetween, a portion of said tines being adapted for contact with said contact surface of said collar assembly to transfer said opposite force thereto.

6. The extractor system of claim 1, wherein said extractor assembly further comprises:

a resilient member disposed between said frame and said drill bit and being deformable by application of said urging force to said drill bit so that release of the deformation urges said drill bit from said object.

7. The extractor system of claim 6, wherein said resilient member comprises:

a spring operatively disposed between said frame and said first component.

8. The extractor system of claim 1, further comprising:

at least one fastener for releasably securing said frame to said object.

9. A method of extracting a drill bit lodged in a tree, said method comprising:

mounting a frame to the tree;

installing an extractor assembly on a frame;

operating said extractor assembly such that a backward urging force is applied against said drill bit; and rotating said drill bit in reverse of its drilling direction while said extractor assembly urges against said drill bit.

10. The method of claim 9, further comprising:

operating said extractor assembly such that a resilient member is deformed by the urging force applied against said drill bit.

11. The method of claim 9, wherein said extractor assembly comprises an extraction screw mechanism, said extractor assembly comprising:

an elongated threaded first component removably mountable to said frame in said extracting configuration wherein said first component extends from front to back relative to said frame; and a threaded second component adapted for rotational engagement with said first component; and wherein said first and second components are configured such that rotating one of said first or second components in a particular direction causes the other component to move opposite the forward axial drilling direction and provide said urging force; and wherein operating said extractor assembly comprises rotating one of said first or second components.

12. The method of claim 11, wherein said extraction screw mechanism is positionable parallel to said drill bit, and wherein:

said first component is a lead screw; and said second component is a carriage assembly, said carriage assembly being configured for screw engagement with said lead screw, said carriage assembly having an extension extending radially with respect to said lead screw when engaged with said lead screw, said extension being adapted to transfer said urging force to said drill bit; and wherein operating said extractor assembly comprises rotating said lead screw.

13. The method of claim 12, further comprising:

rotating said lead screw such that a spring disposed between said lead screw and said frame is compressed by said carriage assembly urging against said drill bit.

14. A system for drilling into an object with a drill bit, said system comprising:

a frame having a front and back orientation and being positionable in at least a drilling configuration;

a drive assembly removably mountable to said frame, said drive assembly comprising a screw mechanism adapted to convert a portion of rotational force to forward axial force and to transfer said forward axial force to a drill bit in communication therewith, said screw mechanism being removable from said frame when said drill bit is partially drilled into said object; and an extractor assembly removably mountable to said frame and adapted to impart an urging force against a drill bit opposite the forward axial direction of said screw mechanism.

15. The system of claim 14, wherein said extractor assembly comprises an extraction screw mechanism in communication with said drill bit, said extractor assembly comprising:

an elongated threaded first component removably mountable to said frame in said extracting configuration wherein said first component extends from front to back relative to said frame; and a threaded second component adapted for rotational engagement with said first component; and wherein said first and second components are configured such that rotating one of said first or second components in a particular direction causes the other component to move opposite the forward axial drilling direction and provide said urging force.

16. The system of claim 15, wherein said extraction screw mechanism is positionable parallel to said drill bit, and wherein:

said first component is a lead screw; and said second component is a carriage assembly, said carriage assembly being configured for screw engagement with said lead screw, said carriage assembly having an extension extending radially with respect to said lead screw when engaged with said lead screw, said extension being adapted to transfer said urging force to said drill bit.

17. The system of claim 16, further comprising:

a collar assembly securable to said drill bit and adapted to provide a contact surface extending radially from said drill bit for transfer of said force from said carriage assembly.

18. The system of claim 14, further comprising:
a rotating drive for supplying said rotational force, said rotating drive adapted for releasable engagement with said elongated member.

19. A method of drilling an object comprising:
mounting a frame on said object, said frame being adapted for positioning a drill bit against said object;
positioning a drill bit on said frame against said object;
mounting a drive assembly for rotating said drill bit on said frame, said drive assembly comprising a screw mechanism in direct or indirect communication with said drill bit, wherein said screw mechanism is adapted to convert a portion of a source of rotational force provided to said drive assembly to rotate said drill bit to forward axial force and transfer said forward axial force to said drill bit;
supplying a source of rotational force to said drive assembly to rotate said drill bit and to provide forward axial force thereto through said screw mechanism;
interrupting said supply of rotational force and removing said screw mechanism after said drill bit engages said object;
resuming the supply of rotational force to said drive assembly;
reversing the direction of said source of rotational force while applying an urging force against said drill bit opposite the direction of said forward axial force.

* * * * *